United States Patent
Guenther et al.

(10) Patent No.: US 9,243,983 B2
(45) Date of Patent: Jan. 26, 2016

(54) EMISSIONS TEST SYSTEM AND METHOD

(76) Inventors: Mark Guenther, Novi, MI (US); Dan Carpenter, Waterford, MI (US); Jarret Zablocki, St. Clair Shores, MI (US); Fredric Schmidt, Saline, MI (US); Richard Thomas Rooney, Brighton, MI (US); Timothy Alfred Nevius, Saline, MI (US); Scott Thomas Porter, Ann Arbor, MI (US); Leslie Hill, Kenilworth (GB)

( * ) Notice: Subject to any disclaimer, the term of this patent is extended or adjusted under 35 U.S.C. 154(b) by 607 days.

(21) Appl. No.: 13/588,428

(22) Filed: Aug. 17, 2012

(65) Prior Publication Data

US 2012/0304737 A1 Dec. 6, 2012

Related U.S. Application Data

(60) Division of application No. 12/952,710, filed on Nov. 23, 2010, now Pat. No. 8,272,248, which is a continuation of application No. 12/757,361, filed on Apr. 9, 2010, now abandoned.

(51) Int. Cl.
*G01M 15/10* (2006.01)
*G01N 1/22* (2006.01)

(52) U.S. Cl.
CPC ...... *G01N 1/2252* (2013.01); *G01N 2001/2255* (2013.01)

(58) Field of Classification Search
CPC .................................................. G01M 15/10
USPC ........ 73/23.31–23.33, 31.03, 863.01, 863.03, 73/863.51, 863.55, 864.34, 864.81, 863.31
See application file for complete search history.

(56) References Cited

U.S. PATENT DOCUMENTS

| | | | | |
|---|---|---|---|---|
| 4,302,815 A | * | 11/1981 | Tedeschi | F02B 77/083 123/682 |
| 5,616,850 A | * | 4/1997 | Sage | G01N 27/122 422/95 |
| 5,756,360 A | | 5/1998 | Harvey et al. | |
| 5,821,435 A | * | 10/1998 | Kojima | B01D 53/30 73/863.01 |
| 6,412,333 B2 | * | 7/2002 | Inoue | G01N 1/2252 73/23.2 |
| 6,443,021 B2 | * | 9/2002 | Hanashiro | 73/863.11 |
| 6,490,937 B2 | * | 12/2002 | Hanashiro | G01N 1/2258 73/863.11 |
| 7,141,090 B2 | | 11/2006 | Marek et al. | |
| 7,559,262 B2 | | 7/2009 | Silvis et al. | |
| 8,181,543 B2 | | 5/2012 | Silvis et al. | |
| 8,813,538 B2 | * | 8/2014 | Carlson | G01N 33/0016 73/23.31 |
| 2010/0000339 A1 | * | 1/2010 | Silvis | G01N 1/2252 73/863.01 |
| 2012/0210803 A1 | | 8/2012 | Silvis et al. | |

OTHER PUBLICATIONS

William M. Silvis, R. Neal Harvey, Allen F. Dageforde, A CFV Type Mini-dilution Sampling System for Vehicle Exhaust Emissions Measurement, 1998 Society of Automotive Engineers, Inc., 9 pgs.

* cited by examiner

*Primary Examiner* — Hezron E Williams
*Assistant Examiner* — Hoang Nguyen
(74) *Attorney, Agent, or Firm* — Brooks Kushman P.C.

(57) ABSTRACT

An emission test system may include at least one controller configured to determine, directly or indirectly, a quantity of diluted exhaust sample in a container at the completion of an emissions test, and to cause additional diluent gas to be added to the container based on the determined quantity.

11 Claims, 10 Drawing Sheets

EMISSIONS TEST SYSTEM AND METHOD

CROSS-REFERENCE TO RELATED APPLICATION

This application is a divisional of application Ser. No. 12/952,710, filed Nov. 23, 2010, which is a continuation of application Ser. No. 12/757,361, filed Apr. 9, 2010, the contents of each of which are hereby incorporated by reference herein.

BACKGROUND

Traditional methods for sampling vehicle exhaust include constant volume sampler (CVS) and container mini-diluter (BMD) techniques. CVS techniques dilute the entire exhaust output from the vehicle, meter the mixture and take a proportional sample for measurement. BMD techniques reverse this process by first metering a small sample, diluting it to a fixed dilution ratio, and then filling a sample bag proportional to the engine exhaust flowrate.

SUMMARY

An engine emissions test system may include a mixing junction configured to mix at least a portion of an exhaust sample from the engine with a diluent gas to form a diluted exhaust sample and a container configured to collect at least a portion of the diluted exhaust sample. The system may also include at least one controller configured to determine a quantity of the diluted exhaust sample collected within the container and to cause additional diluent gas to be added to the container based on the determined quantity such that the quantity of gas within the container is increased to at least a target quantity sufficient to flush a gas analyzer configured to analyze the gas collected within the container.

A method for emissions may include collecting an exhaust sample from an engine, diluting the exhaust sample with a diluent gas to form a diluted exhaust sample, collecting at least a portion of the diluted exhaust sample within a container, determining a quantity of the diluted exhaust sample within the container, and causing additional diluent gas to be added to the container based on the determined quantity to increase the quantity of gas within the container to a target quantity.

The method may further include flushing a gas analyzer with gas from the container.

Diluting the exhaust sample with a diluent gas may be performed only when the engine is operating.

An emissions test system may include a container configured to collect diluted or un-diluted exhaust gas from an engine. The system may also include at least one controller configured to determine a parameter that depends on at least one of a quantity of gas within the container and a concentration of gas within the container and to cause diluent gas to be added to the container based on the determined parameter to increase the quantity of gas within the container to at least a target quantity.

The at least one controller may be further configured to cause a gas analyzer to be flushed with gas from the container such that a concentration of gas within the gas analyzer is generally equal to a concentration of gas within the container.

An exhaust sampling system may include a pre-fill gas source having a pre-fill gas, a sampling conduit configured to collect exhaust gas and diluent gas, and a sample container fluidly connected to the sampling conduit and the pre-fill gas source. The system may further include a controller programmed to run a test procedure in which a sample of the exhaust gas and diluent gas is collected in the sample container. The controller may be configured to (i) send a command that fills the sample container with a desired amount of pre-fill gas prior to the test procedure, with the pre-fill gas remaining in the sample container during the test procedure, (ii) determine a quantity of the pre-fill gas, exhaust gas and diluent gas in the sample container after the test procedure, and (iii) send a command that adds additional gas to the sample container based on the determined quantity to increase the quantity of gas within the sample container to a target.

The test system may further include a pump; the controller sending the command that fills the sample container with a desired amount of pre-fill gas prior to the test procedure to the pump to pre-fill the sample container.

The desired amount of pre-fill gas may correspond to a quantity of pre-fill gas maintaining a dew point within the sample container during the test procedure below an undesired dew point.

The desired amount of pre-fill gas may be calculated based upon at least one of a CVS test flow rate, a dew point of the pre-fill gas, a dew point of the diluent gas, and an anticipated test dew point. quantities relating to the sample container.

A method of collecting an exhaust gas sample may include pre-filling a sample container with a pre-fill gas, collecting an exhaust sample in the sample container with the pre-fill gas remaining in the sample container, determining a quantity of the pre-fill gas and exhaust sample in the sample container and adding post-fill gas to the sample container based on the determined quantity to increase the quantity of gas within the sample container to a target quantity. Collecting an exhaust sample in the sample container with the pre-fill gas remaining in the sample container may include collecting a sample that has been diluted based upon a dilution ratio corresponding to:

$$\frac{prefillconvol + dilutionvol + postfillconvol}{samplevol} + 1$$

where prefillconvol, dilutionvol, postfillconvol and samplevol respectively correspond to the pre-fill gas, dilution gas, post-fill gas and sample exhaust gas quantities relating to the sample container.

DETAILED DESCRIPTION

Figure 1:
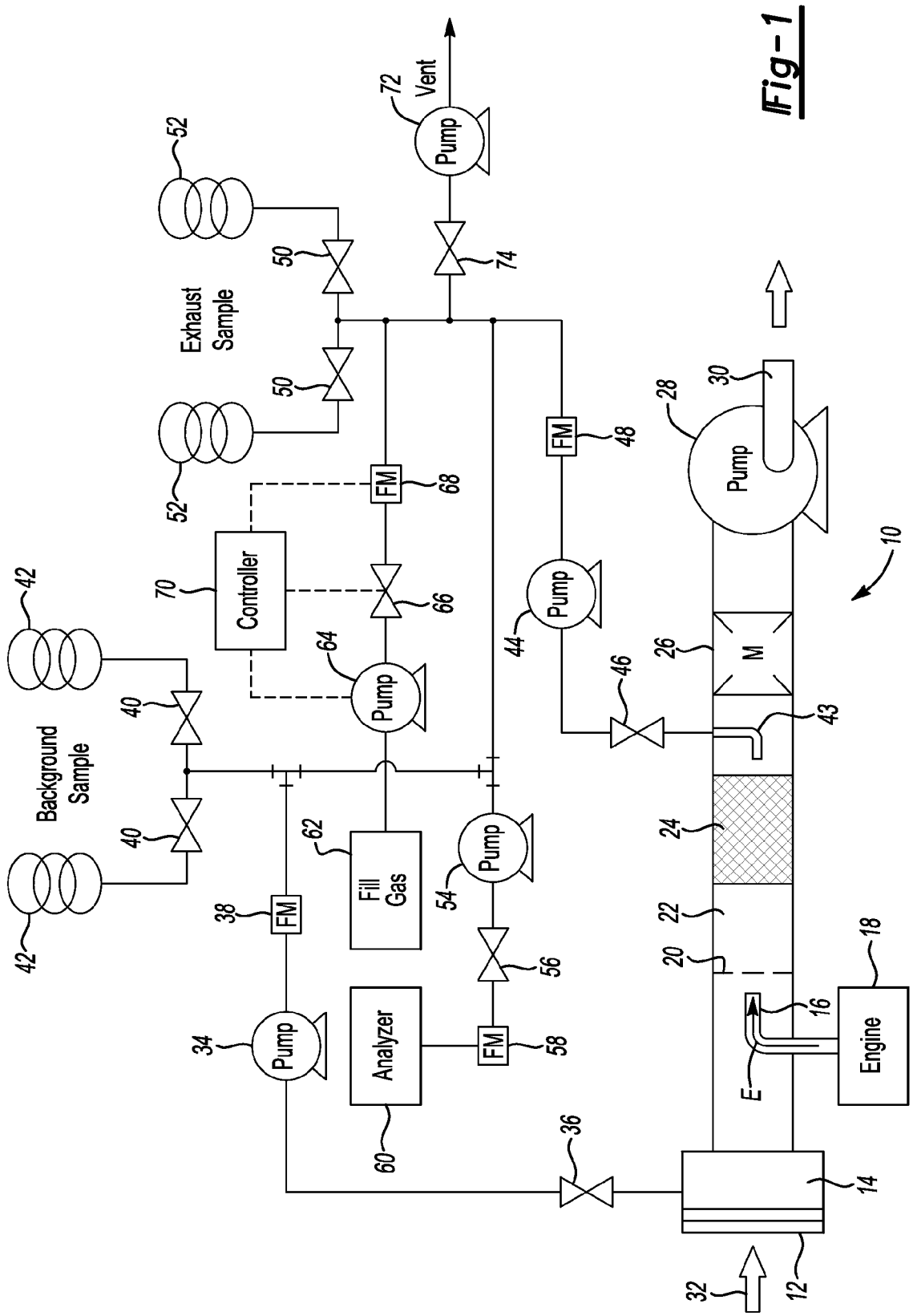
FIG. 1 is a schematic view of an embodiment of a CVS emissions test system.

Emission samples from alternatively powered vehicles, such as hybrid electric vehicles, plug-in hybrid electric vehicles, etc., collected in sample containers via traditional CVS and BMD techniques may be difficult to accurately analyze. The volume (or mass) of the gases collected may be insufficient to flush a gas analyzer such that a concentration of the gases collected in the sample container is generally equal to a concentration of gases within the gas analyzer. (A gas analyzer that has not been effectively flushed may contaminate the sample with other gases—resulting in incorrect readings.)

Unlike conventionally powered vehicles, an engine of an alternatively powered vehicle may be ON for only a portion of an emissions test cycle—resulting in less gas volume (or mass) in the sample container. Testing has revealed that the frequency and duration of engine ON time for a particular alternatively powered vehicle may vary from vehicle to vehicle and test to test. As a result, it may be difficult to predict with accuracy when and for how long the engine of an alternatively powered vehicle will be ON during an emissions test cycle.

Systems implementing CVS and BMD collection techniques typically attempt to prevent condensation of water in the sample collected. Water condensation may change the concentration and volume of the sampled gases—affecting the accuracy of any analysis thereon. Condensation may be prevented, for example, by diluting the sample with diluent as it is collected and/or by pre-filling the sample container with diluent prior to sample collection.

The quantity of gases collected using conventional CVS or BMD techniques may be insufficient to flush a gas analyzer as explained above. This container under-fill issue may be prevented by pre-filling the sample container with diluent to account for any shortage. As explained below, the amount of pre-fill necessary to prevent container under-fill is likely more than the amount of pre-fill necessary to prevent condensation. As a result, pre-filling to prevent container under-fill may also prevent condensation. There is, however, a high risk of over-dilution when pre-filling to prevent container under-fill.

Certain embodiments disclosed herein address the container under-fill issue by topping off, post-test, the sample container with gas (post-fill gas) such that there is sufficient gases in the container to flush a gas analyzer and/or sufficient gases in the container to permit the gas analyzer to achieve a stable response (e.g., a measured value that changes less than 1% over some minimum period of time). The amount of post-test diluent (post-fill gas) added may be based on the difference between the quantity of gases necessary to flush a gas analyzer and the actual quantity of gases in the sample container. This difference may be the target amount of post-test diluent to be added to the sample container. This target amount, of course, may be limited to the maximum volume of the sample container.

To determine the quantity of gases necessary to flush a gas analyzer, parameters that may be considered include, for example, the gas analyzer flow rate (the minimum amount of flow specified by the gas analyzer) and the container analysis time (the time required for the gas analyzer to achieve a gas concentration generally equal to that of the sample container). For example, the flow rate (e.g., 15 L/min.) may be multiplied by the analysis time (e.g., 2 min.) to calculate the amount of gases necessary to flush the gas analyzer (e.g., 30 L).

Parameters that may be considered to determine the actual quantity of gases in the sample container may include, for example, the pre-fill gas volume (if any) and the sample volume collected. For example, the mass flows into the sample container may be measured and then integrated over time. These parameters may be summed to determine the amount of gases within the sample container.

The container concentrations prior to post-test top off may be calculated from the analysis en masse calculations for sample and top off diluent in the container. The resulting dilution ratios may be optimized to minimize analysis errors.

Post-test top off may also be performed, in some embodiments, in conjunction with pre-filling to avoid condensation. This process reduces the extent (or risk) of over-dilution as compared with techniques that use pre-fill to prevent container under-fill. To illustrate, consider a situation where pre-filling is performed to prevent condensation during the testing of an alternatively powered vehicle. In this example, a 45 L container is used to collect the sample and 25 L of gas is needed to flush a gas analyzer (that will analyze the sample) such that the concentration of gases within the container is generally equal to the concentration of gases within the gas analyzer.

One may estimate that 7 L of sample will be collected in a container. Based on this estimate, 10 L of pre-fill gas is needed to prevent condensation within the container. This estimate may be off by as much as (or more than) 700%, however, for the reasons explained above. For example, the actual amount of sample collected may range from 0.5 L to 30 L. Assuming only 5 L of sample is actually collected, 10 L of gas will need to be added post-test to achieve the target quantity of 25 L. The ratio of sample to pre-fill and post-fill gas, in this example, is 5 to 20.

Now consider a situation where pre-filling is performed to prevent container under-fill. The same 45 L container and 25 L target quantity will be used. One may again estimate that 7 L of sample will be collected but may, nevertheless, have to pre-fill the container assuming that only the minimum (0.5 L for example) of sample will be collected. That is, 24.5 L of pre-fill gas is needed. Assuming 5 L of sample is actually collected, the ratio of sample to pre-fill gas, in this example, is 5 to 24.5 (as compared with the 5 to 20 ratio above). Thus, the extent (or risk) of over-dilution is less for the pre-fill/post-fill technique as compared with the exclusive pre-fill technique.

If the minimum (or near minimum) is not assumed in the exclusive pre-fill technique, the situation may arise where the container does not have the 25 L of gas needed to flush the gas analyzer. For example, if the pre-fill gas quantity is determined based on the 7 L estimate, 18 L of pre-fill gas would be added. If less than 7 L of sample is actually collected, there will be less than 25 L of gases in the container at the completion of the test.

A schematic view of an exhaust sampling system 10 is shown in FIG. 1. In this disclosure, like numerals are used to indicate generally like elements. The system 10 includes a make-up air inlet 12 that includes a filter 14. The inlet 12 provides make-up air 32 to a sampling conduit that also receives exhaust from a tailpipe 16 of an engine 18. The make-up air 32 and exhaust E pass through a mixing plate 20 to promote homogeneous mixing of the make-up air 32 and exhaust E as it flows through a tunnel 22 prior to sampling. A mixing plate, however, may not be necessary to achieve homogeneous mixing. A constant volume of the mixture is drawn through the sampling conduit by a pump 28. A heat exchanger 24 is used, in one example, to maintain the mixture at a desired temperature thus maintaining constant mass flow. The mixture is measured by a measuring device 26, prior to being expelled by the pump 28 through a discharge 30, to determine the quantity of mixture flowing through the sampling conduit. It should be understood that the system 10 is only exemplary and that many modifications can be made and still fall within the scope of the claims.

The engine 18 is run through a test procedure to determine the quantity of exhaust byproducts that the engine 18 produces. For the example system 10 shown, only a small portion of the exhaust E is sampled for subsequent analysis. As the amount of exhaust E produced by the engine 18 during the test procedure fluctuates, the make-up air 32 provides the remainder of the volume. The amount of byproducts in the sample is so small at times, that the components in the make-up air can impact the test results. To this end, a pump 34 draws an amount of make-up air into background containers 42 during the test procedure so that the effects of the make-up air can be taken into account. Valves 36, 40 regulate the filling of make-up air 32 into the background containers 42, and the flow meter 38 measures the amount of make-up air collected within the background containers 42.

A sampler 43 collects a small sample of the mixture for collecting into sample containers 52. One or more sample containers 52 may be used, and filling of the sample containers may be scheduled during various periods of the test procedure. A pump 44 draws the sample through a valve 46 and flow meter 48. Valves 50 regulate the filling of the sample containers 52. After the sample containers 52 have collected the samples, an analyzer 60 analyzes the contents of the sample containers 52 and background containers 42 to determine the amount of various combustion byproducts. A pump 54 flows the sample through valve 56 and flow meter 58. It should be understood that more or fewer pumps, valves and flow meters than shown could be used.

A controller 70 communicates during the test procedure with the various pumps 28, 34, 54, 64, 72, valves 36, 40 46, 50, 56, 66, 74 and flow meters 38, 48, 58, 68 to obtain readings and direct their operation. All of the connections between the controller 70 and these components are not shown for clarity.

In one example, one or more of the sample containers 52 is pre-filled with dry gas to prevent any peaks in dew point during the test procedure that would lead to undesired condensation. A source of gas 62 is shown schematically in FIG. 1. An amount of gas is pumped into one or more of the sample containers 52 prior to the collection of the exhaust sample. The controller 70 commands the pump 64 and valve 66 to fill a desired amount of gas to a desired sample container 52 to prevent condensation in the sample container 52. The pre-fill may also incorporate other means to fill the container such as a compressed gas source. The flow meter 68 measures the amount of gas.

Figure 2:
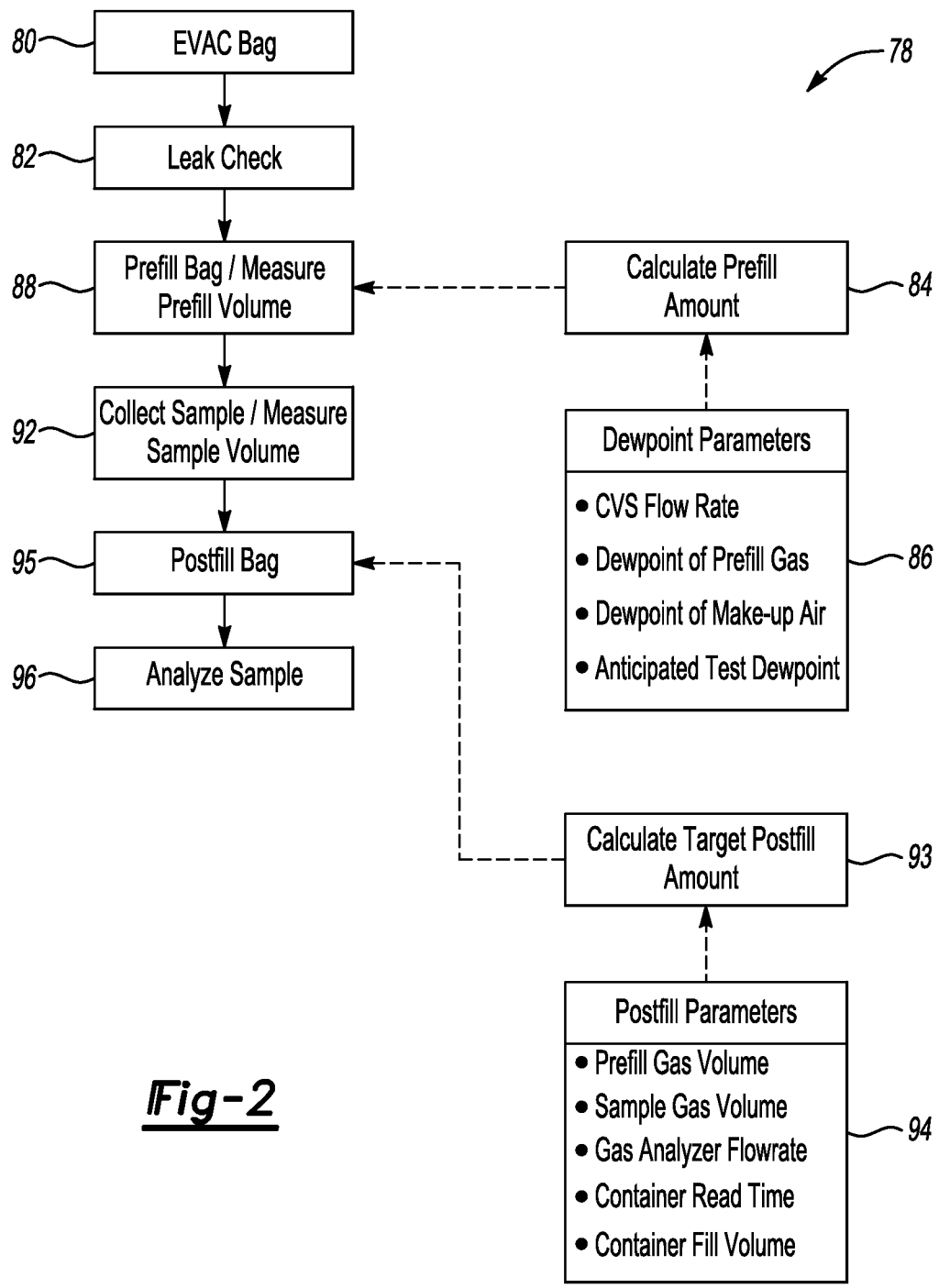
FIG. 2 is a flow chart depicting an example algorithm for use with the system of FIG. 1.

An example test procedure 78 is shown in FIG. 2. The amount of pre-fill gas needed to prevent condensation is calculated at block 84 based upon one or more of the following (indicated at block 86): CVS test flow rate, dew point of the pre-fill gas, dew point of the make-up air, and anticipated test dew point within the sample container 52. Calculations are performed based upon the various factors of each test to determine the minimum amount of pre-fill gas required to avoid condensation. This approach may minimize further dilution of the sample. The containers susceptible to condensation would be filled with dry clean air prior to the sampling (filling of the container). According to this disclosure, the initial peak of wet gas is compensated for by the dry air, thus preventing condensation.

The sample containers 52 and ambient containers 42, as well as any intervening conduits, are evacuated through vent 74 using pump 72, as indicated at block 80. The system 10 is leak checked (block 82), and the sample containers 52 are pre-filled with a predetermined amount of pre-fill gas, as indicated at block 88. The amount of pre-fill gas is measured. The exhaust sample is collected and its mass and/or volume measured in the sample containers 52 during the test procedure with the pre-fill gas remaining in the sample containers 52, as indicated at block 92. As the sample containers 52 are filled during the test procedure, the dew point of the predetermined amount of pre-fill gas prevents the exhaust sample from condensing within the sample containers 52.

The post-fill volume is calculated, as described above, at block 93 based upon one or more of the following (indicated at block 94): pre-fill gas volume, sample gas volume, gas analyzer flow rate, container read time and container fill volume. This post-fill volume, when added to the containers 52, permits the containers 52 to achieve a target quantity of gas or gases sufficient to flush or scrub the gas analyzer 60 such that a concentration of the gas or gases within the sample containers 52 is generally equal to a concentration of gas or gases within the gas analyzer 60.

The sample containers 52 are next filled with at least the calculated post-fill volume of gas as indicated at block 95.

The contents of the sample containers 52 and ambient containers 42 can then be analyzed to determine the amount of byproducts within the sample, as indicated at block 96.

In one example, the same "zero grade" or "instrument grade" air that is typically used to initially calibrate the system 10 can be used to pre-fill and/or post-fill the sample containers 52. As a result, the pre-fill and/or post-fill feature can be incorporated into a traditional CVS with very little modification and expense. Alternatively, ambient air can be used to pre-fill and/or post-fill the sample containers 52. Using ambient air may be desirable since it makes accounting for the pre-fill and/or post-fill air's effects at the analysis stage of the test simpler. The analytical equations set forth in the Code of Federal Regulations for test procedures are such that accounting, for example, for pre-fill ambient air is more straightforward. Using zero grade air instead of ambient air requires modifications to those equations, which may not be desired by some users. For example, using zero air requires using dilution ratio equations similar to those used for a BMD system to determine the concentration necessary to use traditional CVS equations. It should be understood that any number of suitable substances may be used to pre-fill and/or post-fill the sample containers 52.

Figure 3:
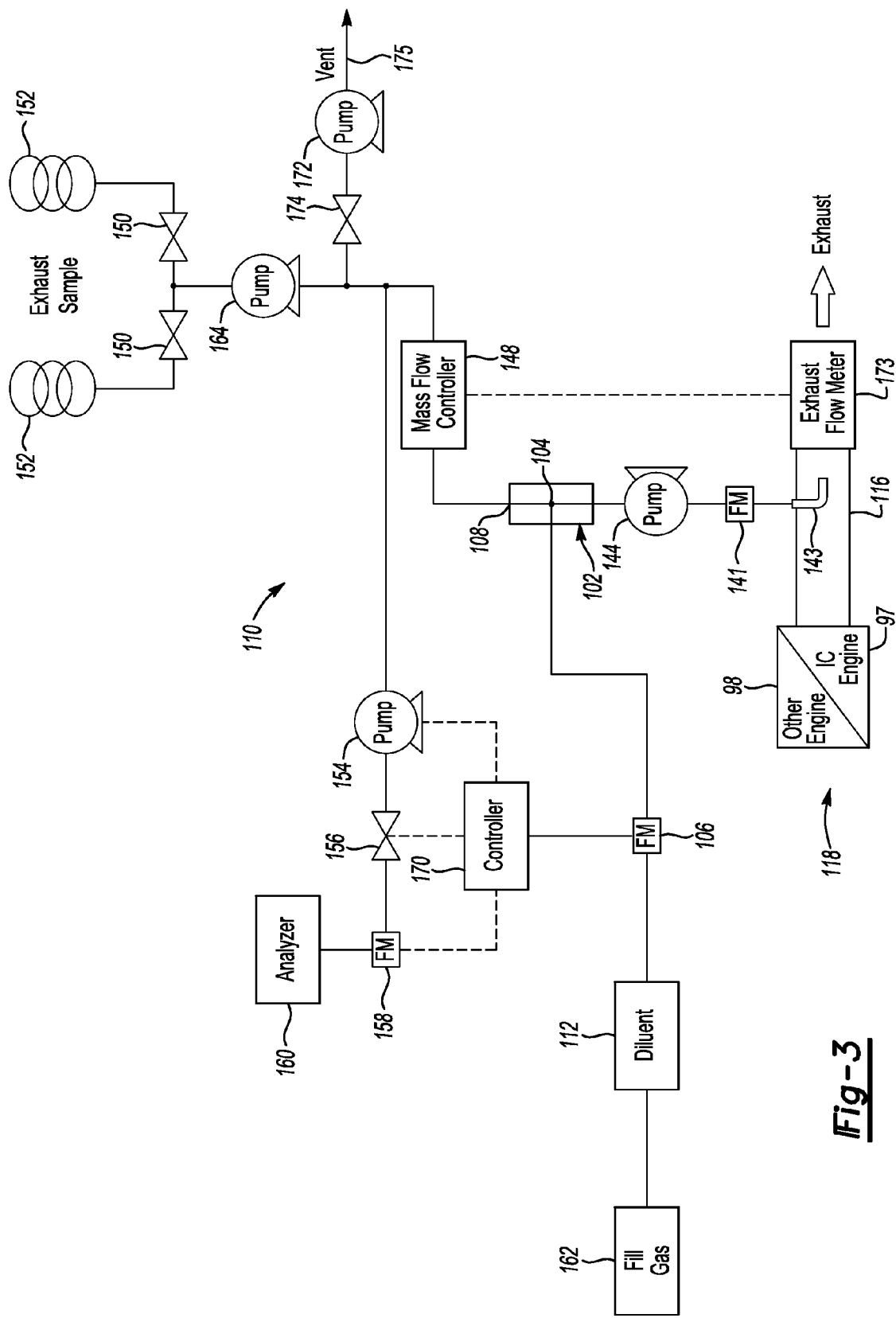
FIG. 3 is a schematic view of an embodiment of a BMD emissions test system.

A schematic view of another exhaust sampling system 110 is shown in FIG. 3. The system 110 illustrates a BMD sampling system in which the exhaust sample is diluted at a fixed rate and the exhaust gas sample is collected in proportion to the exhaust flow from the engine 118. In the example, the engine 118 includes an internal combustion engine 97 and another engine 98 (such as an electric motor) that together comprise the propulsion unit for a hybrid vehicle. The other engine 98 may be used to propel the vehicle in varying degrees throughout vehicle operation. As a result, there may be periods of operation when the engine 118 expels little or no exhaust through its tailpipe 116 when the other engine 98 is in use.

The system 110 includes a "mini-diluter" having a probe or sampler 143. The sampler 143 collects a small sample of exhaust gas from the tailpipe 116. The total flow rate of exhaust gas is measured by the exhaust flow meter 173. The sample exhaust gas is drawn into a sampling unit 102 by a pump 144. The sampling unit 102 includes a mixer 104. A diluent 112 is introduced to the sampling unit 102 at the mixer 104 where it commingles with the sample exhaust gas to produce a diluted exhaust gas that has been diluted at a generally constant dilution ratio that is supplied to a diluted exhaust gas outlet 108. In one example, the diluent 112 is nitrogen or zero air. The diluent 112 is measured by a flowmeter 106. The sample exhaust gas flow corresponds to a difference between a total exhaust gas flow measured by a flowmeter 148, which receives the diluted exhaust gas from the outlet 108, and the flowmeter 106. Alternatively, flow controllers, for example, may be used to control the sample exhaust gas and diluted exhaust gas. Other arrangements are also possible. In the example shown, the exhaust gas sample is measured directly by a flowmeter 141.

The engine 118 is run through a test procedure to determine the quantity of exhaust byproducts that the engine 118 produces. For the example system 110 shown, only a small portion of the exhaust is sampled for subsequent analysis. As the amount of exhaust produced by the engine 118 during the test procedure fluctuates, the diluent 112 provides the remainder of the volume.

The sampler 143 collects a small sample of the mixture for collecting into sample containers 152. One or more sample containers 152 may be used, and filling of the sample containers may be scheduled during various periods of the test procedure. Valves 150 regulate the filling of the sample containers 152. After the sample containers 152 have collected the samples, an analyzer 160 analyzes the contents of the sample containers 152 to determine the amount of various combustion byproducts. A pump 154 flows the sample through valve 156 and flow meter 158. It should be understood that more or fewer pumps, valves and flow meters than shown could be used.

A controller 170 communicates during the test procedure with the various pumps 144, 154, 164, 172, valves 150, 156, 174 and flow meters 106, 141, 148, 158, 173 to obtain readings and direct their operation. All of the connections between the controller 170 and these components are not shown for clarity.

In one example, one or more of the sample containers 152 is pre-filled with dry gas to prevent water from condensing while the sample is collected. While this pre-fill gas may be of an amount sufficient to prevent water condensation, it may not be of an amount necessary to account for any container under-fill that results from the engine 97 being on for only portions of the test cycle (and as explained above, it may be difficult to predict how much gas will be collected during the test cycle).

A source of fill gas 162 is shown schematically in FIG. 3. A common nitrogen source can be used for both the diluent 112 and the fill gas 162. In an example, the fill gas 162 is nitrogen. An amount of pre-fill gas is pumped into one or more of the sample containers 152 prior to the collection of the exhaust sample. The controller 170 commands the pump 164 to fill a desired amount of pre-fill gas to a desired sample container 152 to sufficiently fill the sample container 152 so that water does not condense during sample collection. The pre-fill may also incorporate other means to fill the container such as a compressed air source. The flow meter 106 measures the amount of pre-fill gas. Using the same flow meter 106 to measure the pre-fill gas and the diluent during the test procedure may minimize calibration error.

Figure 4:
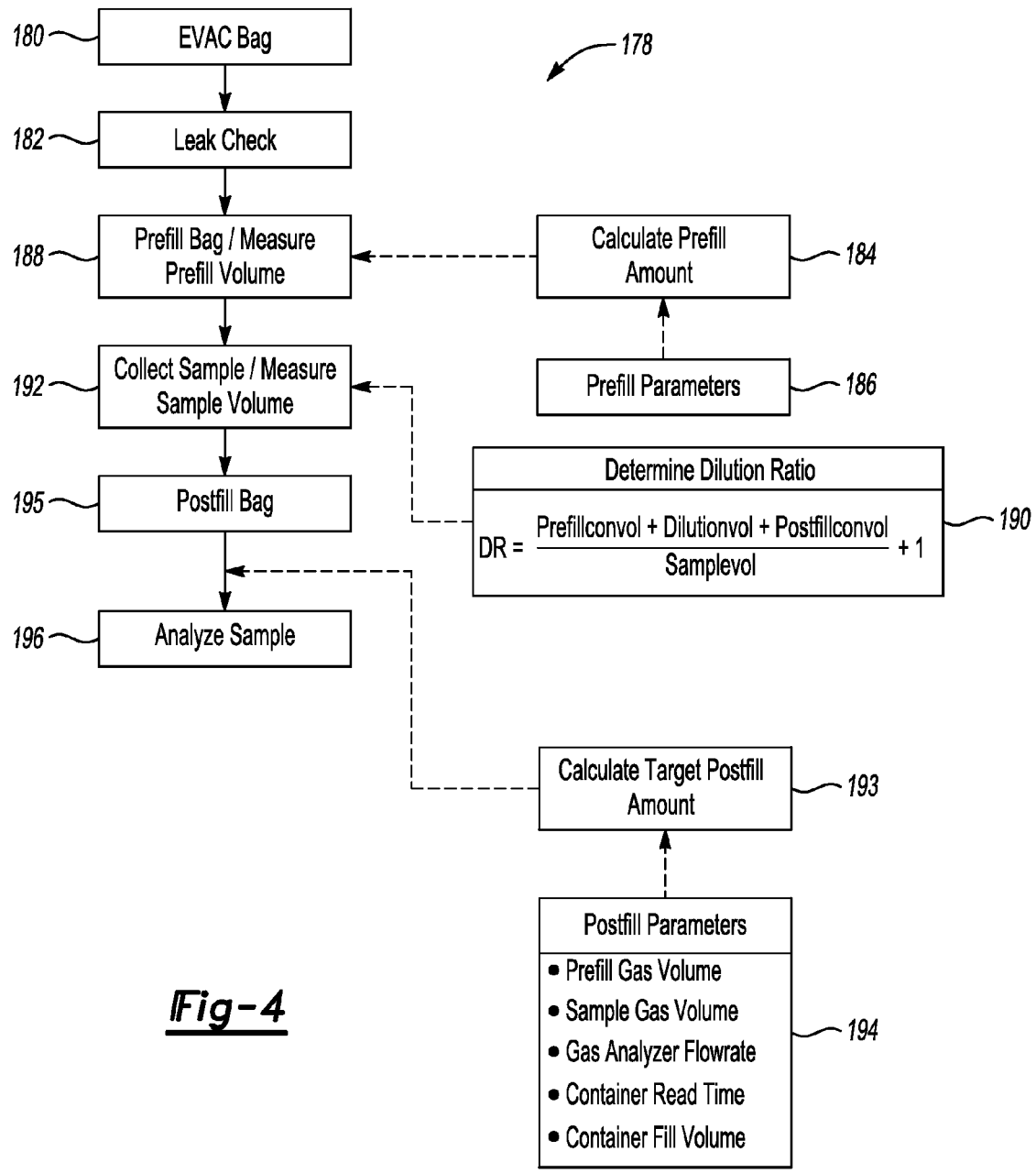
FIG. 4 is a flow chart depicting an example algorithm for use with the system of FIG. 2.

An example test procedure 178 according to the disclosure is shown in FIG. 4. The amount of pre-fill gas needed to prevent water from condensing within the containers 152 is calculated at block 184 based upon parameters (block 186) similar to those described with reference to block 86 (FIG. 2).

The sample containers 152, as well as any intervening conduits, are evacuated through vent 175 using pump 172, as indicated at block 180. The system 110 is leak checked (block 182), and the sample containers 152 are filled with a predetermined amount of pre-fill gas, as indicated at block 188. The amount of pre-fill gas is measured. The exhaust sample is collected and its mass and/or volume measured in the sample containers 152 during the test procedure with the pre-fill gas remaining in the sample containers 152, as indicated at block 192.

The post-fill gas volume is calculated at block 193 based upon parameters (block 194) similar to those described with reference to block 94 (FIG. 2). This post-fill volume, when added to the containers 152, permits the containers 152 to achieve a target quantity of gas or gases sufficient to flush or scrub the gas analyzer 160 such that a concentration of the gas or gases within the sample containers 152 is generally equal to a concentration of gas or gases within the gas analyzer 160.

The sample containers 152 are next filled with at least the calculated post-fill volume of gas as indicated at block 195.

In certain BMD systems, the dilution ratio is measured as the ratio sample flow to total flow of the BMD and integrated over the test procedure. In the example system 110, the dilution ratio integrates the amount of dilution gas in a given container 152 from the pre-filled process plus the amount of diluent used during and after the test procedure. The dilution ratio, DR, for the system 110 is as follows (block 190):

$$DR = \frac{prefillconvol + dilutionvol + postfillconvol}{samplevol} + 1$$

where prefillconvol, dilutionvol, postfillconvol and samplevol respectively correspond to the pre-fill gas, diluent, post-fill gas and sample exhaust gas volumes relating to a given sample container 152. The contents of the sample containers 152 can then be analyzed to determine the amount of byproducts within the sample, as indicated at block 196. The diluent flow 112 through flow meter 106 may be set to zero, such that the exhaust sample within the container 152 is only diluted by fill gas 162 within the container 152 (i.e., dilutionvol=0).

In one example, the same "zero grade" or "instrument grade" air that is typically used to initially calibrate the system 110 can be used to pre-fill and/or post-fill the sample containers 152. As a result, the pre-fill and/or post-fill feature can be incorporated into a traditional BMD with very little modification and expense. Alternatively, ambient air can be used to pre-fill and/or post-fill the sample bas 152. Using ambient air may be desirable since it makes accounting for the pre-fill air's effects at the analysis stage of the test simpler. The analytical equations set forth in the Code of Federal Regulations for test procedures are such that accounting, for example, for pre-fill ambient air is more straightforward. Using zero grade air instead of ambient air requires modifications to those equations, which may be undesired by some users. It should be understood, however, that any number of suitable substances may be used to pre-fill and/or post-fill the sample containers 152.

Figure 5:
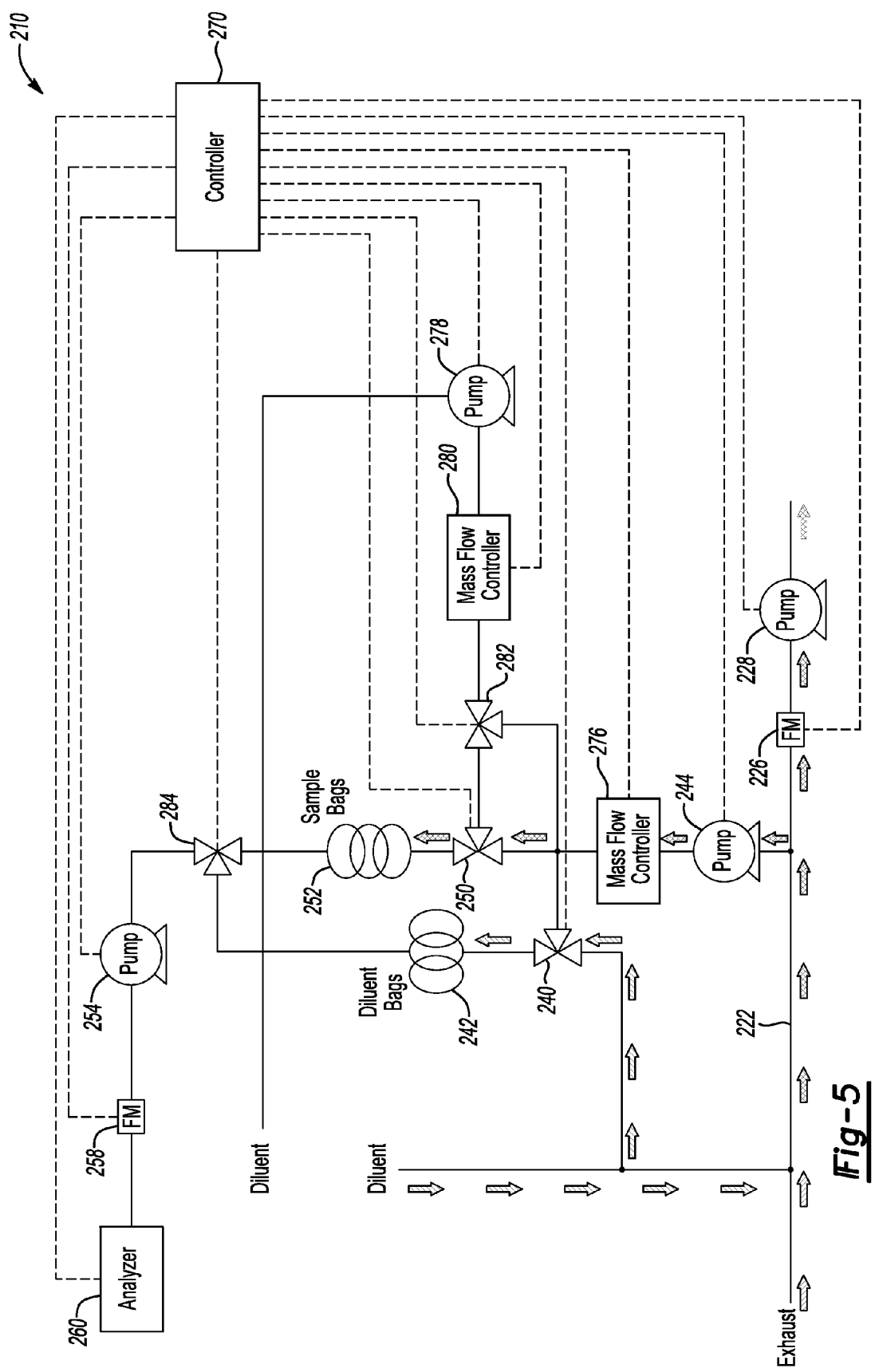
FIGS. 5, 6 and 7 are schematic views of another embodiment of a CVS emissions test system.
Figure 6:
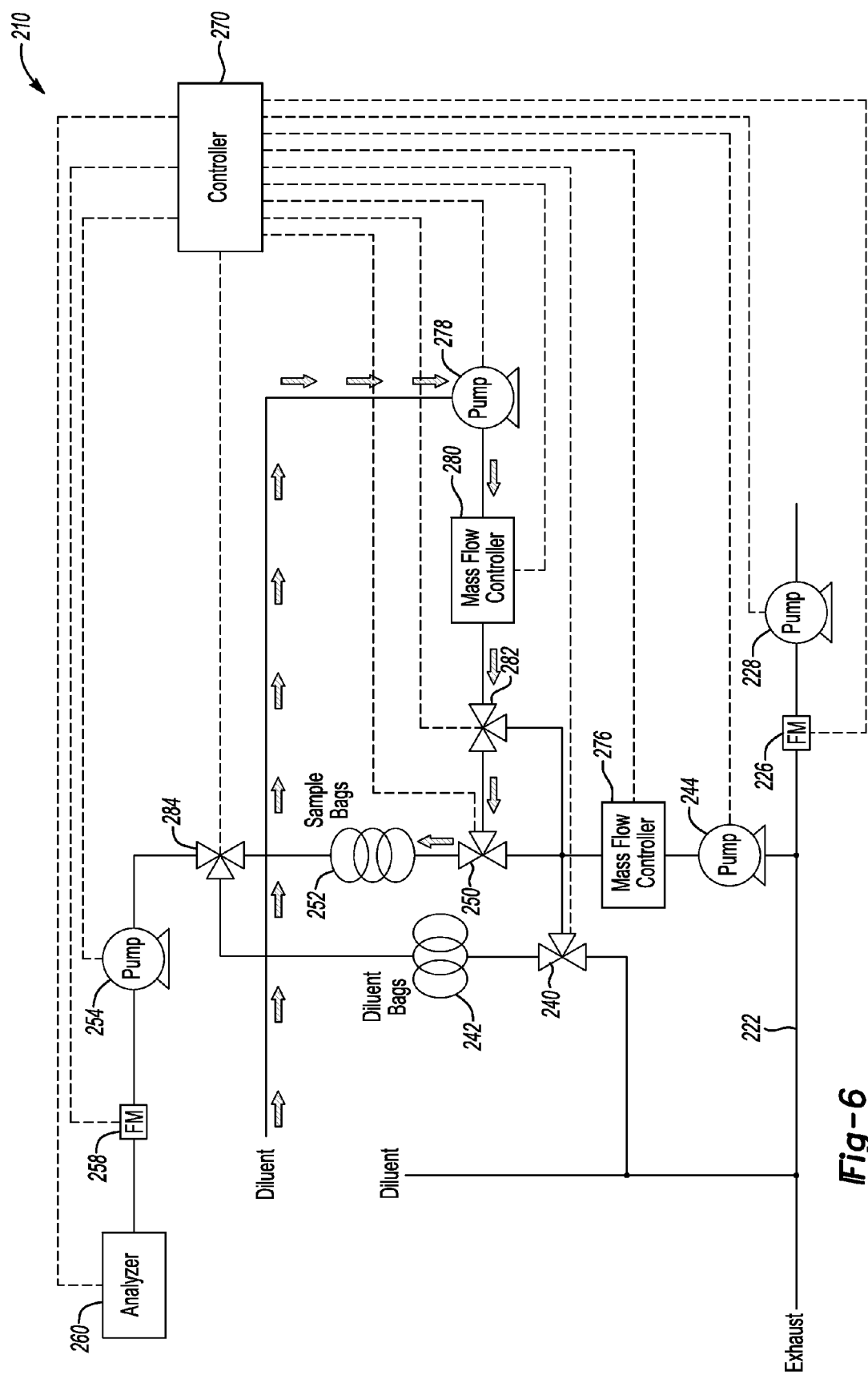
Figure 7:
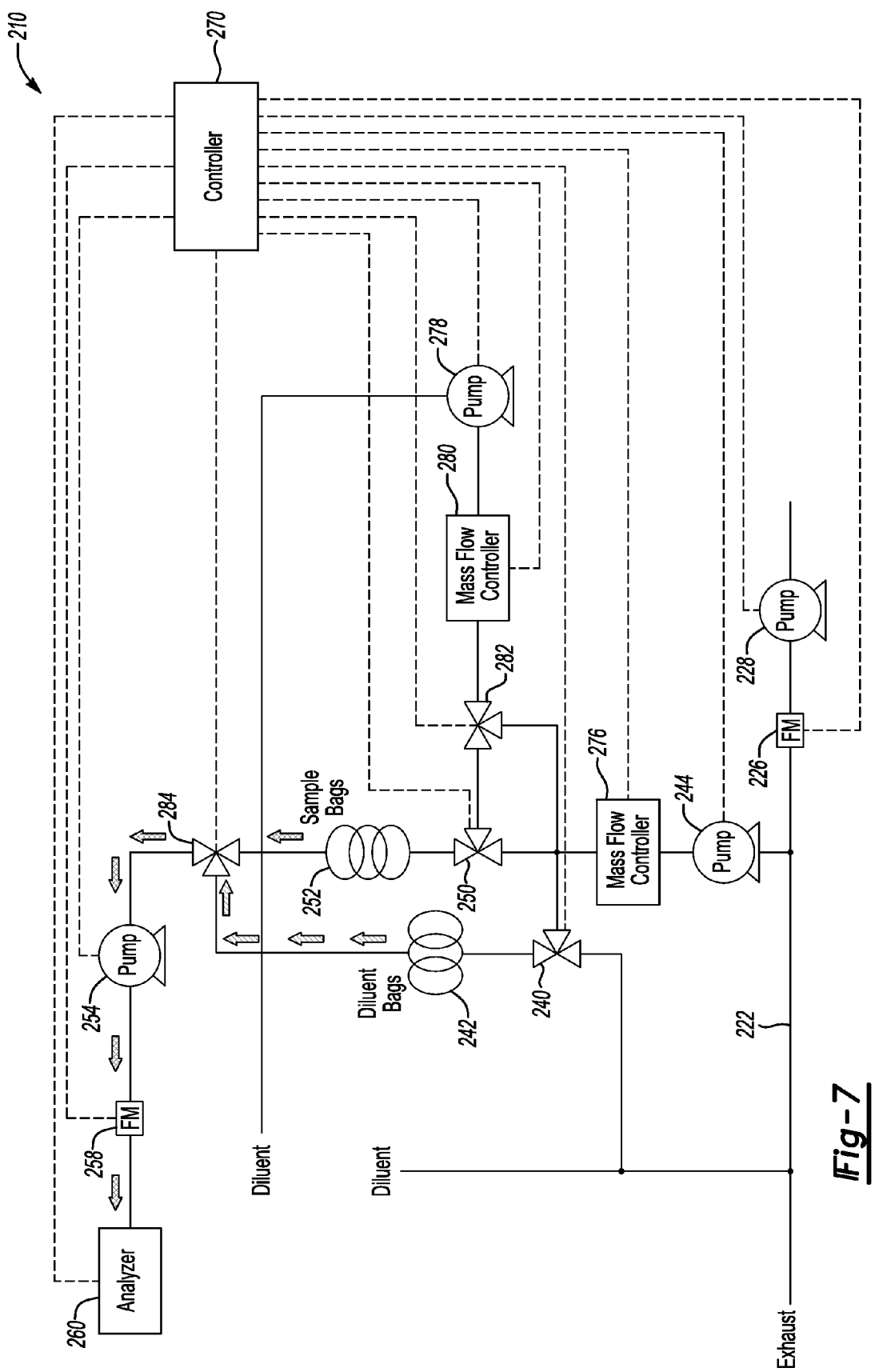

A schematic view of another CVS emissions test system 210 is shown in FIGS. 5, 6 and 7. Arrows indicate the direction of gas flow during the emissions test (FIG. 5), during the post-test top off of the containers 252 (FIG. 6), and during the gas analysis phase. During the emissions test, the controller 270 controls and/or receives information from the pumps 228, 244, valves 240, 250, and mass flow controller 276 such that diluent fills the diluent containers 242 and the diluted exhaust sample fills the sample containers 252. (No pre-fill of the containers 252 is performed.) During the post-test top off of the containers 252, the controller 270 controls and/or receives information from a pump 278, mass flow controller 280 (any flow measurement and/or control system, however, may be used; for example, venturi-type, etc.), and valves 250, 282 such that diluent fills the sample containers 252 to a target amount.

As explained above, this target amount may be the amount necessary to flush the analyzer 260 such that a concentration of gases within the analyzer 260 is generally equal to a concentration of gases within the sample containers 252. The amount of diluent added to the sample containers 252 under the direction of the controller 270 may depend on the difference between the amount of gas needed to flush the analyzer 260 and the amount of gas collected in the sample containers 252 during the emissions test. This collected gas amount may be determined based on measurements of the mass flow controller 276 taken during the emissions test cycle.

During the gas analysis phase, the controller 270 controls and/or receives information from the pump 254, flow meter 258 and valve 284 such that gases from at least one of the sample containers 252 is used to sweep the gas analyzer 260. Once swept, gases from the containers 242, 252 may be analyzed by the gas analyzer 260 in a known fashion.

Figure 8:
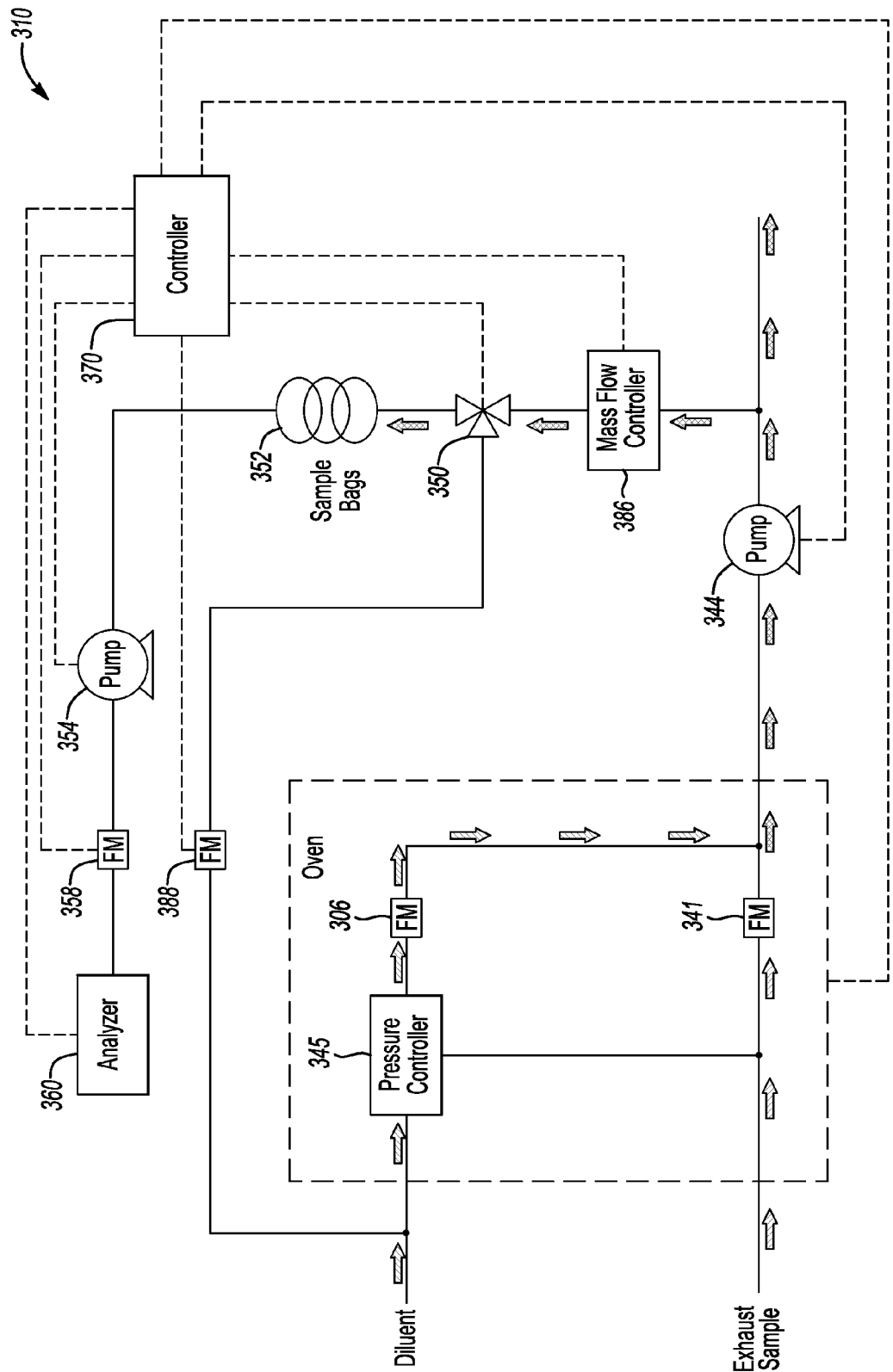
FIGS. 8, 9 and 10 are schematic views of another embodiment of a BMD emissions test system.
Figure 9:
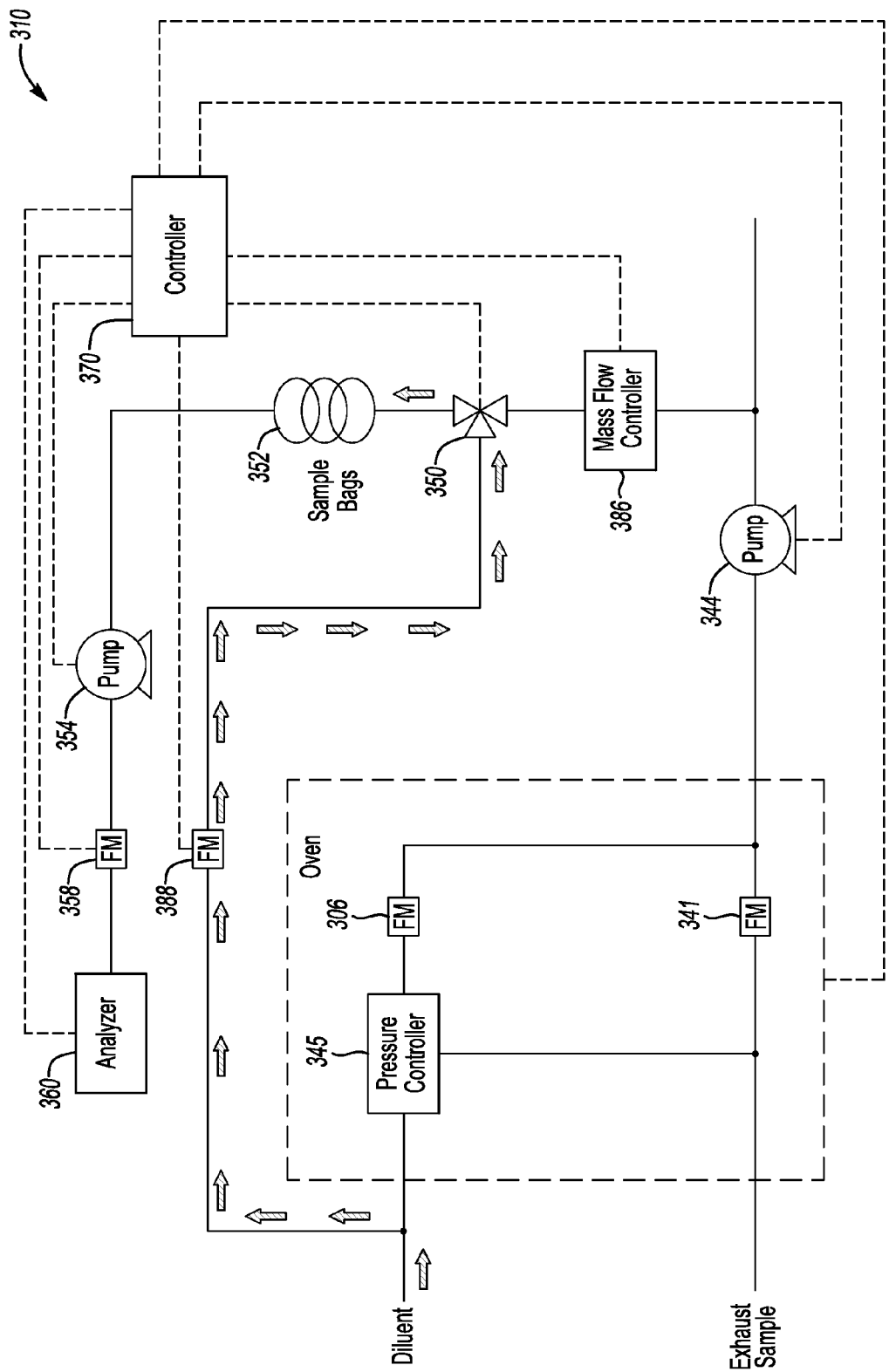
Figure 10:
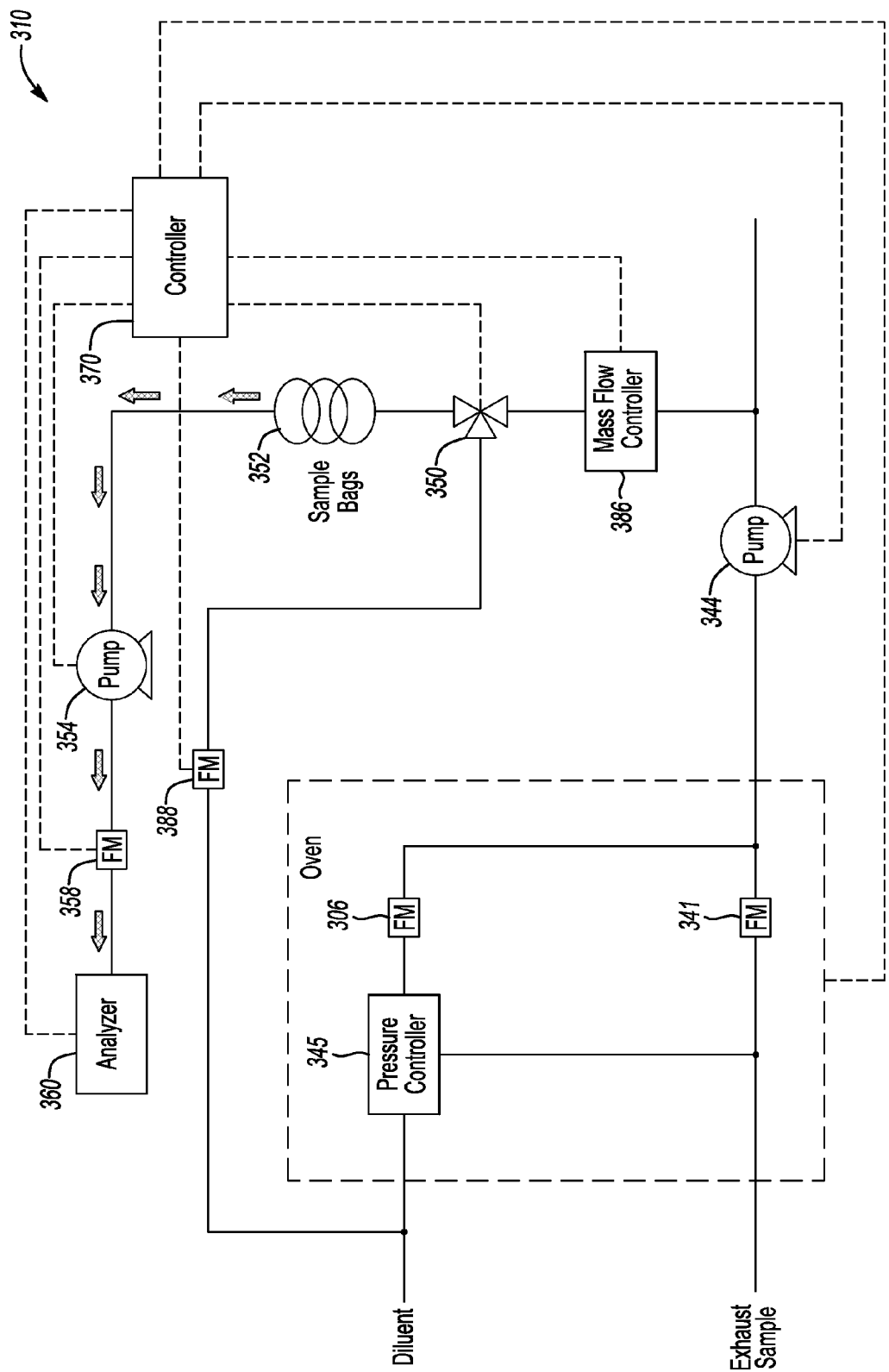

A schematic view of another BMD emissions test system 310 is shown in FIGS. 8, 9 and 10. Arrows indicate the direction of gas flow during the emissions test (FIG. 8), during the post-test top off of the containers 352 (FIG. 6), and during the gas analysis phase. During the emissions test, the controller 370 controls and/or receives information from flow meters 306, 341, pump 344, pressure controller 345, valve 350 and mass flow controller 386 such that diluted exhaust sample fills the sample containers 352. (No pre-fill of the containers 352 is performed.) During the post-test top off of the containers 352, the controller 370 controls and/or receives information from the valve 350 and flow meter 388 such that diluent fills the sample containers 352 to at least a target amount. As explained above, this target amount may be an amount of gas necessary to flush the analyzer 360. During the gas analysis phase, the controller 370 controls and/or receives information from the pump 354 and flow meter 358 such that gas from at least one of the sample containers 352 is used to sweep the gas analyzer 360. Once swept, gas from the containers 352 may be analyzed by the gas analyzer 360.

As apparent to those of ordinary skill, the algorithms disclosed herein may be deliverable to a processing device, which may include any existing electronic control unit or dedicated electronic control unit, in many forms including, but not limited to, information permanently stored on non-writable storage media such as ROM devices and information alterably stored on writeable storage media such as floppy disks, magnetic tapes, CDs, RAM devices, and other magnetic and optical media. The algorithms may also be implemented in a software executable object. Alternatively, the algorithms may be embodied in whole or in part using suitable hardware components, such as Application Specific Integrated Circuits (ASICs), state machines, controllers or other hardware components or devices, or a combination of hardware, software and firmware components.

While embodiments of the invention have been illustrated and described, it is not intended that these embodiments illustrate and describe all possible forms of the invention. In certain embodiments for example, an emissions test system may include a first flow meter, a second flow meter, and a mixing junction. The first flow meter may be configured to meter exhaust gas from the engine to the mixing junction. The second flow meter may be configured to meter diluent to the mixing junction at a generally constant dilution ratio to obtain a diluted exhaust sample. The test system may also include a sample container configured to collect at least a portion of the diluted exhaust sample proportionally to an exhaust flow rate of the engine. The test system may further include at least one controller configured to determine a quantity of the diluted exhaust sample collected in the container and to cause additional diluent gas to be added to the container based on the determined quantity to increase the quantity of gas within the container to a target quantity sufficient to flush a gas analyzer configured to analyze gas from the container such that a concentration of gas within the gas analyzer is generally equal to a concentration of gas within the container.

The at least one controller may be further configured to cause a pre-fill diluent to be added to the sample container before the at least a portion of the diluted exhaust sample is collected.

The at least one controller may be further configured to determine a quantity of the pre-fill diluent added to the sample container.

The at least one controller may be further configured to cause additional diluent gas to be added to the container based on the determined quantity of the pre-fill diluent added to the sample container.

An emissions test system, in certain embodiments, may include a mixing junction configured to dilute an entire exhaust flow of the engine with a diluent to form a diluted exhaust flow, a flow meter configured to measure a flow rate of the diluted exhaust flow, a flow controller configured to extract a sample from the diluted exhaust flow proportional to the flow rate of the diluted exhaust flow, and a sample container configured to collect the extracted sample. The test system may further include at least one controller configured to determine a quantity of the extracted sample collected in the sample container and to cause additional diluent to be added to the sample container based on the determined quantity to increase the quantity of gas within the sample container to a target quantity sufficient to flush a gas analyzer configured to analyze gas from the sample container such that a concentration of gas within the gas analyzer is generally equal to a concentration of gas within the container.

The at least one controller may be further configured to cause a pre-fill diluent to be added to the sample container before the extracted sample is collected.

The at least one controller may be further configured to determine a quantity of the pre-fill diluent added to the sample container.

The at least one controller may be further configured to cause the additional diluent to be added to the container based on the determined quantity of the pre-fill diluent added to the sample container.

A method of collecting an exhaust gas sample, in certain embodiments, may include pre-filling a sample container with a pre-fill gas, collecting an exhaust sample in the sample container with the pre-fill gas remaining in the sample container, and determining a quantity of the pre-fill gas and exhaust sample in the sample container. The method may further include adding post-fill gas to the sample container based on the determined quantity to increase the quantity of gas within the sample container to a target quantity.

Pre-filling a sample container with a pre-fill gas may include pre-filling the sample container with the pre-fill gas corresponding to a predetermined pre-fill gas amount sufficient to prevent condensation in the sample container.

The predetermined pre-fill gas amount may be determined based upon a CVS test flow rate.

The predetermined pre-fill gas amount may be determined based upon a dew point of the pre-fill gas.

Collecting an exhaust sample in the sample container with the pre-fill gas remaining in the sample container may comprise collecting a sample including the exhaust sample and diluent gas, and the predetermined pre-fill gas amount may be determined based upon a dew point of the diluent gas.

The predetermined pre-fill gas amount may be determined based upon an anticipated test procedure dew point.

Collecting an exhaust sample in the sample container with the pre-fill gas remaining in the sample container may include collecting a sample that has been diluted based upon a dilution ratio corresponding to:

$$\frac{prefillconvol + dilutionvol + postfillconvol}{samplevol} + 1$$

where prefillconvol, dilutionvol, postfillconvol and samplevol respectively correspond to the pre-fill gas, dilution gas, post-fill gas and sample exhaust gas quantities relating to the sample container.

A method for emissions testing, in certain embodiments, may include causing diluted or un-diluted exhaust gas from an engine to be collected within a container, determining a parameter that depends on at least one of a quantity of gas within the container and a concentration of gas within the container, and causing diluent gas to be added to the container based on the determined parameter to increase the quantity of gas within the container to at least a target quantity.

The method may further include flushing a gas analyzer with gas from the container such that a concentration of gas within the gas analyzer is generally equal to a concentration of gas within the container.

Additionally, other techniques for determining the quantity of post-fill gas to be added to a sample container include, for example, placing the sample container (e.g., bag) within a sealed container and measuring the change in pressure within the sealed container as the sample container fills with pre-fill gas (if any) and sample gas during test. The pressure within the sealed container depends on the quantity (e.g., volume) of gas within the sample container. A look-up table may be generated in advance that correlates the sealed container pressure with the quantity of gas within the sample container. The amount of post-fill gas may thus be determined via the sealed container pressure. The sample container, alternatively, may be weighed before pre-fill (if any) and after test to determine the quantity of gas within the sample container.

The quantity of gas within the sample container, in other embodiments, may be determined based on a measured raw concentration, a measured concentration in the sample container, and information regarding total exhaust volume (from, for example, an engine control unit or exhaust flow meter). The concentration measurements may be direct or indirect (e.g., measuring the thermal conductivity of the sample container, etc.)

As an example, the sample container volume collected from an engine can be determined using a measured or given un-diluted exhaust gas concentration (e.g., 13.4% $CO_2$), a measured or given diluted exhaust gas concentration (e.g., 2.2% $CO_2$), and the integrated engine exhaust volume measured or given during a test procedure (e.g., 9.2 $ft^3$). The sampled dilution ratio may be determined by dividing the un-diluted concentration by the diluted concentration (e.g., 13.4%/2.2%=6.09). Given that certain BMD and/or CVS systems are configured to proportionally sample exhaust at a specified rate (e.g., 1.0 L per 10 $ft^3$ of engine exhaust), the amount of diluted exhaust sample in the sample container can be calculated (e.g., 9.2 $ft^3 \times 1.0$ L/10 $ft^3$=0.92 L).

Still other embodiments may be used in conjunction with other engine types such as fuel cell, sterling, etc., and/or collect/measure un-diluted or diluted exhaust gas. Moreover, the containers discussed herein may be conduits, bags, cylinders with movable pistons, etc.

The words used in the specification are words of description rather than limitation, and it is understood that various changes may be made without departing from the spirit and scope of the invention. Also, it should be understood that the operations of the algorithms and/or methods described herein may be performed in any suitable order or in parallel as desired.

What is claimed:

1. An exhaust sampling system comprising:
   a pre-fill gas source having pre-fill gas;
   a sampling conduit configured to collect exhaust gas and diluent gas;
   a sample container fluidly connected to the sampling conduit and the pre-fill gas source; and
   a controller programmed to run a test procedure in which a sample of the exhaust gas and diluent gas is collected in the sample container, the controller configured to (i) send a command that fills the sample container with a desired amount of the pre-fill gas prior to the test procedure, with the pre-fill gas remaining in the sample container during the test procedure, (ii) determine a quantity of the pre-fill gas, exhaust gas and diluent gas in the sample container after the test procedure, and (iii) send a command that adds post-fill gas to the sample container based on the determined quantity to increase gas quantity within the sample container to a target quantity.

2. The system of claim 1 further comprising a pump, the controller sending the command that fills the sample container with the desired amount of the pre-fill gas prior to the test procedure to the pump to pre-fill the sample container.

3. The system of claim 1 wherein the desired amount of the pre-fill gas corresponds to a quantity of the pre-fill gas maintaining a dew point within the sample container during the test procedure below an undesired dew point.

4. The system of claim 3 wherein the desired amount of the pre-fill gas is calculated based upon at least one of a CVS test flow rate, a dew point of the pre-fill gas, a dew point of the diluent gas, and an anticipated test dew point.

5. A method of collecting an exhaust gas sample comprising:
   by a controller,
      pre-filling a sample container with pre-fill gas;
      collecting an exhaust sample in the sample container with the pre-fill gas remaining in the sample container;
      determining a quantity of the pre-fill gas and exhaust sample in the sample container; and
      adding post-fill gas to the sample container based on the determined quantity to increase gas quantity within the sample container to a target quantity, wherein collecting an exhaust sample in the sample container with the pre-fill gas remaining in the sample container includes collecting a sample that has been diluted based upon a dilution ratio corresponding to:

$$\frac{prefillconvol + dilutionvol + postfillconvol}{samplevol} + 1$$

where prefillconvol, dilutionvol, postfillconvol and samplevol respectively correspond to the pre-fill gas, dilution gas, post-fill gas and sample exhaust gas quantities relating to the sample container.

6. The method of claim 5 wherein the pre-fill and post-fill gases are the same.

7. A method of collecting an exhaust gas sample comprising:
by a controller,
pre-filling a sample container with a desired amount of pre-fill gas prior to a test procedure in which a sample of exhaust gas and diluent gas is collected in the sample container, wherein the pre-fill gas remains in the sample container during the test procedure, and
adding post-fill gas to the sample container based on a determined quantity of the pre-fill gas, exhaust gas and diluent gas in the sample container after the test procedure to increase gas quantity within the sample container to a target quantity.

8. The method of claim 7, wherein the desired amount of the pre-fill gas corresponds to a quantity of the pre-fill gas maintaining a dew point within the sample container during the test procedure below an undesired dew point.

9. The method of claim 7, wherein the desired amount of the pre-fill gas is calculated based upon at least one of a CVS test flow rate, a dew point of the pre-fill gas, a dew point of the diluent gas, and an anticipated test dew point.

10. The method of claim 7, wherein the pre-fill and post-fill gases are the same.

11. The system of claim 1 wherein the pre-fill and post-fill gases are the same.

* * * * *